(12) United States Patent
Chou et al.

(10) Patent No.: US 6,218,208 B1
(45) Date of Patent: Apr. 17, 2001

(54) FABRICATION OF A MULTI-STRUCTURE ION SENSITIVE FIELD EFFECT TRANSISTOR WITH A PH SENSING LAYER OF A TIN OXIDE THIN FILM

(75) Inventors: Jung-Chuan Chou, Touliu, Yunlin; Wen-Yaw Chung, Chung-Li; Shen-Kan Hsiung, Chung-Li; Tai-Ping Sun, Chung-Li; Hung-Kwei Liao, Zhu Dong, all of (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/347,226

(22) Filed: Jul. 2, 1999

(51) Int. Cl.[7] .................................................. H01L 21/00
(52) U.S. Cl. .............................................. 438/49; 438/197
(58) Field of Search ............................. 438/49, 104, 288, 438/197

(56) References Cited

U.S. PATENT DOCUMENTS

| | | |
|---|---|---|
| 4,358,274 | 11/1982 | Chase . |
| 4,397,888 * | 8/1983 | Yannopoulos et al. . |
| 4,609,932 | 9/1986 | Anthony . |
| 4,657,658 | 4/1987 | Sibbald . |
| 4,812,220 | 3/1989 | Iida . |
| 5,078,855 * | 1/1992 | Mochizuki et al. . |
| 5,319,226 | 6/1994 | Sohn et al. . |
| 5,407,854 | 4/1995 | Baxter et al. . |

OTHER PUBLICATIONS

Liao et al., "Temperature and Optical Characteristics of Tin Oxide membrane gate ISFET", Dec. 1999, IEEE Transactions on Electron Devices, vol. 46, No. 12, pp. 2278–2281.*

* cited by examiner

Primary Examiner—Charles Bowers
Assistant Examiner—Evan Pert
(74) Attorney, Agent, or Firm—Jacobson, Price, Holman & Stern, PLLC

(57) ABSTRACT

A sensitive material-tin oxide ($SnO_2$) obtained by thermal evaporation or by r.f. reactive sputtering is used as a high-pH-sensitive material for a Multi-Structure Ion Sensitive Field Effect Transistor. The multi-structure of this Ion Sensitive Field Effect Transistor (ISFET) includes $SnO_2/SiO_2$ gate ISFET or $SnO_2/Si_3N_4/SiO_2$ gate ISFET respectively, and which have high performances such as a linear pH sensitivity of approximately 56~58 mV/pH in a concentration range between pH2 and pH10. A low drift characteristics of approximately 5 mv/day, response time is less than 0.1 second, and an isothermal point of this ISFET sensor can be obtained if the device operates with an adequate drain-source current. In addition, this invention has other advantages, such as the inexpensive fabrication system, low cost, and mass production characteristics. Based on these characteristics, a disposal sensing device can be achieved. Thus, this invention has a high feasibility in Ion Sensitive Field Effect Transistor.

11 Claims, 7 Drawing Sheets

FABRICATION OF A MULTI-STRUCTURE ION SENSITIVE FIELD EFFECT TRANSISTOR WITH A PH SENSING LAYER OF A TIN OXIDE THIN FILM

BACKGROUND OF THE INVENTION

1. Field of the Invention

The present invention describes a sensing device-Multi-Structure Ion Sensitive Field Effect Transistor and a method to fabricate it from high-pH-sensing membrane of tin oxide ($SnO_2$) film obtained by thermal evaporation or by r.f. reactive sputtering.

2. Description of the Prior Art

The traditional ion-selecting glass electrode has many advantages, e.g. high linearity, good ion selectivity, high stability. But it has disadvantages such as large volume, high cost and long reaction time. Hon-Sum Wong et al. reported in IEEE Transactions on Electron Devices, Vol. 36 (3), pp. 479–487 (1989) that people tend to replace the traditional ion-selecting glass electrode by an ion-sensitive field effect transistor developed by semiconductor technology.

In IEEE Transactions on Electron Devices, Vol. BME-17 (1), pp.59–63 (1970), Piet Bergveld reported that after stripping off the metal gate in a regular metal oxide semi-conductor field effect transistor, the device was immersed into aqueous solution. The oxide layer on the gate of the device, as an insulating ion sensing membrane, generates different electrical potentials at the contacting interface in contacting with the solution of different pH values. Thus the channel current varies and the pH value of the solution or the concentration of some other ions can be measured. This phenomenon is referred to by Piet Bergveld as ion-sensitive field effect transistor.

In the 1970s, the development and application of ion-sensitive field effect transistor were still in the investigation stage, as reported by D. Yu et al. in Chemical Sensors, J. Sensor & Transducer Tech., Vol. 1, pp.57–62 (1990). But in the 1980s, the research of ion-sensitive field effect transistor had been raised to a new level. The greatly improved areas were in basic theoretical research, key technology or in the research of practical applications. In other words, more than 20–30 different kinds of field effect transistor transistors, measuring various kinds of ions and chemicals based on the structure of ion-sensitive field effect transistor, have been fabricated. As reported by D. Yu et al. in Chemical Sensors, J. Sensor & Transducer Tech., Vol. 2, pp. 51–55 (1992), ion-sensitive field effect transistors have improved greatly in the areas of minimization, modularizing or multifunctioning. The major reason why the ion-sensitive field effect transistor has become so popular globally is that it has the following special advantages that traditional ion-selecting electrodes lack:

1. Miniaturization so that a minute solution measurement can be performed;
2. High input impedance and low output impedance;
3. Fast response; and
4. The process is compatible with metal-oxide semiconductor field-effect transistor technology.

Since, the ion-sensitive field effect transistor has the above advantages, it has attracted research interest of many researchers over the past twenty years. The more important progress in developing this device internationally during these years is described in the following documents.

W. M. Siu et al. reports with physical and theoretical aspects, IEEE Transactions on Electron Devices, ED-26, Vol. 11, pp. 1805–1815 (1979), that silicon dioxide, silicon nitride, tantalum pentoxide, and aluminum oxide can be the sensing membrane of the ion-sensitive field effect transistor.

A. S. Wong in "Theoretical and Experimental Studies of CVD Aluminum Oxide as a pH Sensitive Dielectric for the Back Contacts ISFET Sensor shows that ion-sensitive field effect transistors with different device structure can use the back contact of the ion-sensitive field effect transistor, or amorphous silicon thin film transistor device for ion-sensitive field effect transistor.

D. Yu, in Chemical Sensors, J. Sensor & Transducer Tech., Vol. 2, pp. 51–55 (1992), reported the miniature of the reference electrode.

B. H. Van Der Schoot et al. reported the integration of measurement system and sensory devices in Sensors and Actuators B, Vol. 4, pp. 239–241 (1991). M. Grattarola et al. reported the simulation research of the ion-sensitive field effect transistor in IEEE Transactions on Electron Devices, Vol. 39 (4), pp. 813–819 (1991).

There are reports of differential type of ion-sensitive field effect transistor. Also, the fixing of enzyme on ion-sensitive field effect transistor to sense the functional signal of biological system, (e.g., sensitive to glucose or sensitive to the oxide concentration in blood, etc.). There is a theoretical study of site-binding model. The research of packaging material and the differential type of ion-sensitive field effect transistor, or the research of packaging material.

U.S. Pat. No. 5,319,226 to Sohn et al. is a method of fabricating an ion sensitive field effect transistor with a $Ta_2O_5$ hydrogen ion sensing membrane. In this patent, an r.f. sputtering method is used to fabricate $Ta_2O_5$ membrane on the gate area of the ion-sensitive field effect transistor to form $Ta_2O_5$/silicon nitride/silicon dioxide structure of the ion-sensitive field effect transistor.

U.S. Pat. No. 5,407,854 to Baxter et al. is an ESD Protection of ISFET sensors. A method is described for preventing the drifting of electrons in the ion-sensitive field effect transistor.

U.S. Pat. No. 4,609,932 to Anthony describes nonplanar ion sensitive field effect transistor devices. In this patent, the micromachining technology of a laser drill was applied to form a nonplanar structure of the ion-sensitive field effect transistor.

U.S. Pat. No. 4,812,220 to Iida et al. describes an enzyme sensor for determining a concentration of glutamate. The enzyme-type ion-sensitive field effect transistor was used to detect the concentration of amino acid in foods.

U.S. Pat. No. 4,657,658 to Sibbald is for metal oxide semiconductor ion-sensitive field effect transistor devices. The patent describes one metal-oxide-semiconductor field effect transistor and one ion-sensitive field effect transistor which are used to form the differential pair systematic modular system.

According to a report by Tadayuki in Sensors and Actuators B, Vol. 1, pp. 77–96 (1981), for the ion-sensitive field effect transistor on the gate oxide, the most frequently used hydrogen ion sensing membrane are silicon dioxide, silicon nitride, tantalum pentoxide, and aluminum oxide, etc. For silicon nitride and aluminum oxide film, usually it is better to fabricate by low-pressure chemical vapor deposition. Therefore, the processing steps determine the chemical composition of the material, and also determine the properties of this sensing membrane.

Additionally, since the membrane is deposited by low-pressure chemical vapor deposition, the variation of the process condition is much more complicated, e.g. the flow rate ratio of the mixed gas, the process temperature and the pressure of process, etc. Once these conditions vary, the chemical composition of the membrane will be changed, and the characteristics of the sensing membrane will vary too.

For silicon nitride film, if the processing condition is not good enough such that the oxygen concentration in the film is higher, the property of the characteristics of the membrane will get worse. Furthermore, since the price of low-pressure chemical vapor deposition system is more expensive and the gases in the process are quite toxic, so it's not widespread in applications.

According to the report by R. E. G. Van Hal et al. in *Sensors and Actuators B*, Vol. 24–25, pp. 201–205 (1995), tantalum pentoxide material has the best characteristics for hydrogen ion sensing by r.f. sputtering and the target material of tantalum pentoxide on the gate oxide directly forms the structure of the ion-sensitive field effect transistor. Also, since the target material is used for substrate material directly, the chemical composition of the film is easier to control than those fabricated by low-pressure chemical vapor deposition.

In spite of these difficulties, some international research groups are still making effort to study new types of sensing membrane since this kind of sensing device is quite feasible in practical applications. Those materials that have been studied are: zirconium oxide, titanium oxide, ruthenium oxide, rhodium oxide, iridium oxide, platinum oxide, osmium oxide, etc. But, since the sensing characteristics of these materials is not better than silicon nitride and tantalum pentoxide, etc., they are not widely used in the applications.

SUMMARY OF THE INVENTION

Therefore, the present invention seeks to solve the problems described in the prior art with one kind of sensing membrane material, tin oxide ($SnO_2$). The sensing characteristics of tin oxide is close to tantalum pentoxide. It's fabricated by thermal evaporation or r.f. reactive sputtering. The main advantage of the present invention is that a multi-structure ion sensitive field effect transistor with good characteristics can be fabricated from this kind of sensing membrane: $SnO_2/SiO_2$ multi-structure ion sensitive field effect transistor or $SnO_2/Si_3N_4/SiO_2$ multi-structure ion sensitive field effect transistor.

The further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
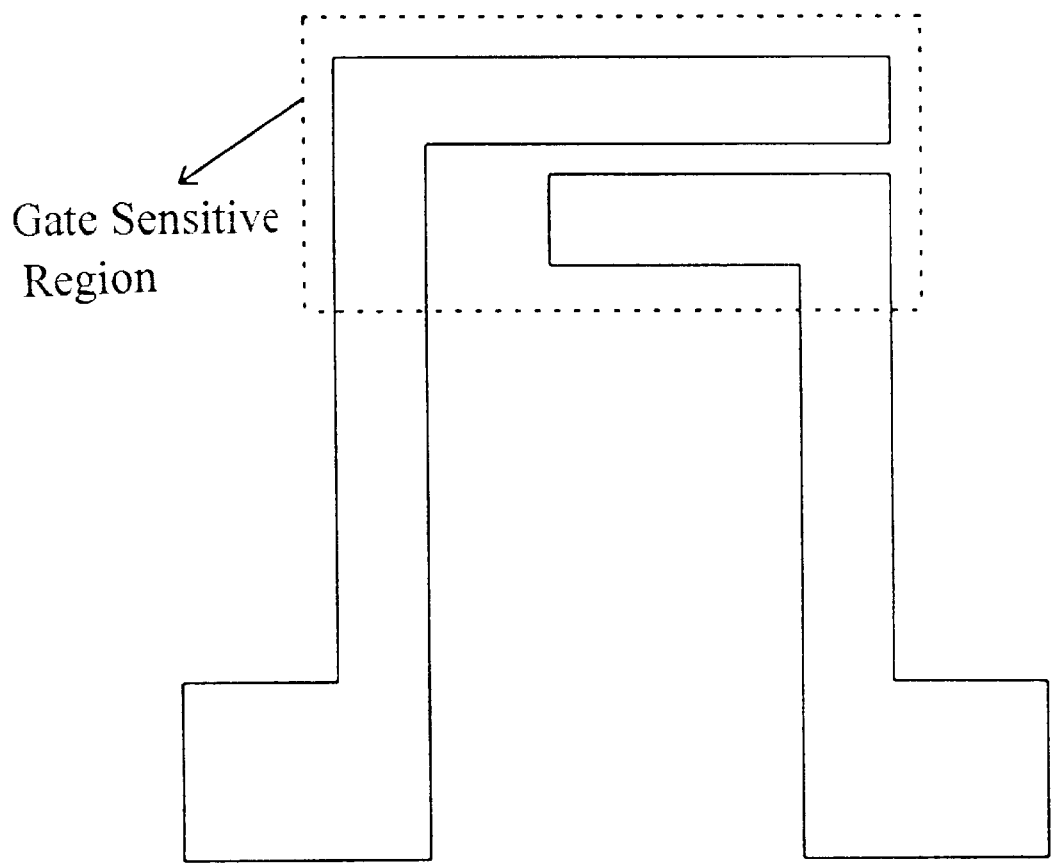
FIG. 1 shows a device structure of the present invention.

The present invention demonstrates a sensing device Multi-Structure Ion Sensitive Field Effect Transistor and the method to fabricate it from high-pH-sensing membrane/tin oxide ($SnO_2$) film obtained by thermal evaporation or by r.f. reactive sputtering.

The present invention demonstrates a sensing device with a multi-structure ion sensitive field effect transistor which is fabricated from high-pH-sensing membrane/tin oxide ($SnO_2$) film. The structure of the multi-structure ion sensitive field effect transistor is formed of $SnO_2/SiO_2$ multi-structure sensing device or $SnO_2/Si_3N_4/SiO_2$ multi-structure sensing device. The thickness of $SiO_2$ and $Si_3N_4$ are about 100 nm, respectively. The thickness of $SnO_2$ is about 150–200 nm. A multi-structure ion sensitive field effect transistor with good characteristics can be fabricated from high-pH-sensing membrane/tin oxide ($SnO_2$) film.

The method of fabricating a multi-structure ion sensitive field effect transistor from high-pH-sensing membrane/tin oxide ($SnO_2$) film, wherein the special feature of the present invention is to fabricate metal-oxide-semiconductor field effect transistor without metal gate on p-type substrate. Also, the method fabricates $SnO_2$ film on the insulating layer of gate by thermal evaporation or by r.f. sputtering to build a multi-structure ion sensitive field effect transistor that can sense the concentration of hydrogen ion. During the process of fabricating $SnO_2$ film on the insulating layer of gate by thermal evaporation or r.f. sputtering, the substrate temperature can be from room temperature to 200° C. and $SnO_2$ film can be annealed in nitrogen, oxygen or argon gas.

The present invention demonstrates a sensing device with a multi-structure ion sensitive field effect transistor which is fabricated from high-pH-sensing membrane/tin oxide (SnO2) film. The process condition is the channel length of this device which is 5 $\mu$m. The channel width is 100 $\mu$m, i.e. there are 81 devices fabricated on one 4 inch wafer in total. The process flow of fabrication is as follows:

1) P-silicon substrate (100), resistivity=8~12 ohm-cm,
2) clean wafer,
3) grow silicon dioxide in wet oxygen (500 nm),
4) apply positive photoresist,
5) mask 1 - - - expose & develop,
6) wet etch silicon dioxide (500 nm),
7) ion implant,
8) mask 2 - - - expose & develop,
9) wet etch silicon dioxide (500 nm) and strip photoresist,
10) silicon dioxide gate 100 nm,
11) mask 3 - - - expose & develop,
12) wet etch silicon dioxide,
13) sputter 500 nm metal gate,
14) mask 4 - - - expose & develop,
15) wet etch aluminum 500 nm and etch photoresist, and
16)
    A.) Fabricate $SnO_2/SiO_2$ double layer ion sensitive field effect transistor on silicon dioxide film by metal mask and thermal evaporated powder;
    B.) Fabricate $SnO_2/Si_3N_4/SiO_2$ multi-layer ion sensitive field effect transistor on $Si_2N_4$ film by metal mask and thermal evaporated powder;
    C.) Fabricate $SnO_2/SiO_2$ double-layer ion sensitive field effect transistor on $SiO_2$ film by metal mask and r.f. sputtering; and D.) Fabricate $SnO_2/Si_3N_4/SiO_2$ multi-layer ion sensitive field effect transistor on $Si_3N_4$ metal mask and r.f. sputtering.

In the above processes, the processing condition of thermal evaporation is shown in table 1. The processing condition of r.f. sputtering is shown in table 2. The annealing condition of $SnO_2$ is shown in table 3. The annealing can be done in nitrogen, oxygen or argon gas. In addition, the characteristics of $SiO_2$ single layer ion sensitive field effect transistor is compared with those of $Si_3N_4/SiO_2$ double layer ion sensitive field effect transistor and $SnO_2$ ion sensitive field effect transistor.

Figure 2:
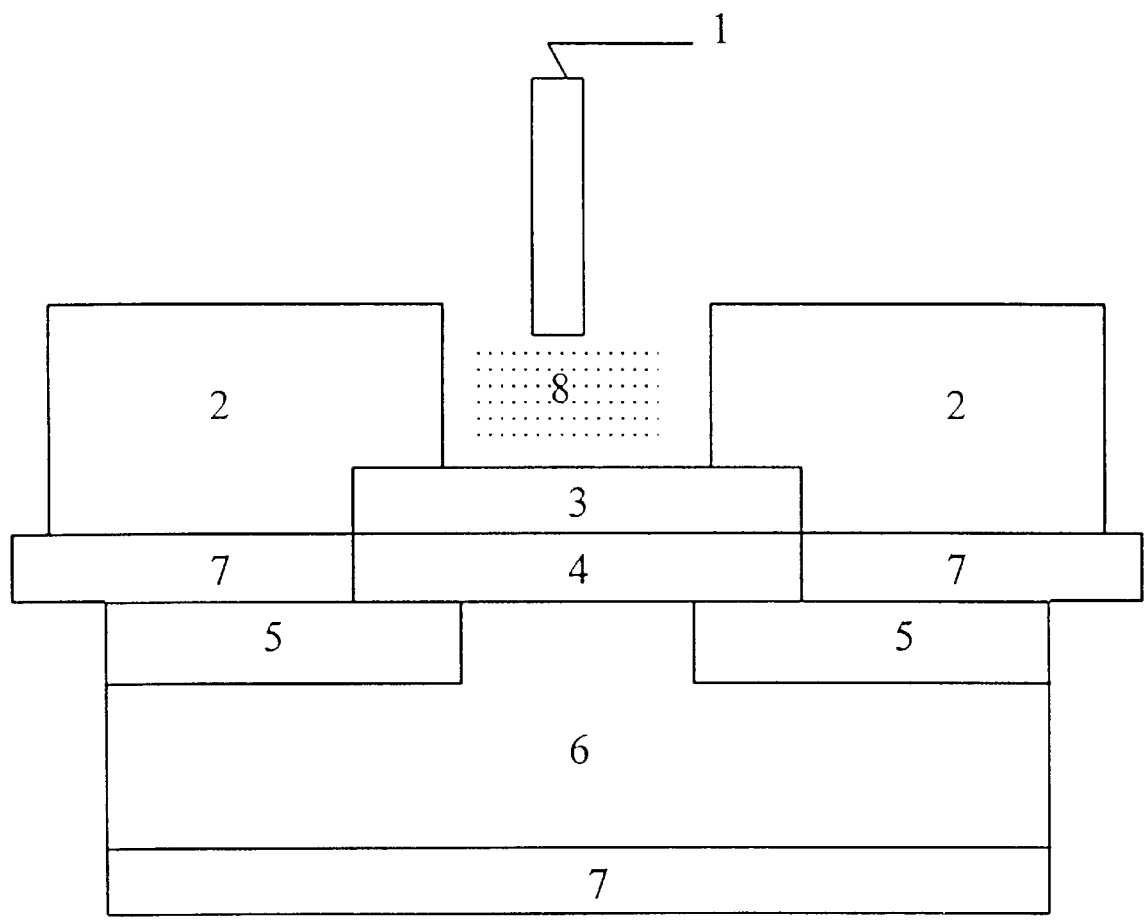
FIG. 2 shows the structure of $SnO_2$ thin film multi-structure ion sensitive field effect transistor.

FIG. 2 shows the structure of $SnO_2$ sensing membrane multi-structure ion sensitive field effect transistor of the present invention. As can be seen from the structure of this figure, the $SnO_2$ thin film multi-structure ion sensitive field effect transistor is obtained by removing the metal gate of the traditional metal-oxide-semiconductor field effect transistor, and replacing it by $SnO_2$ sensing membrane. In addition to that, the metal portion of the source and drain is packaged by epoxy resin.

Figure 3:
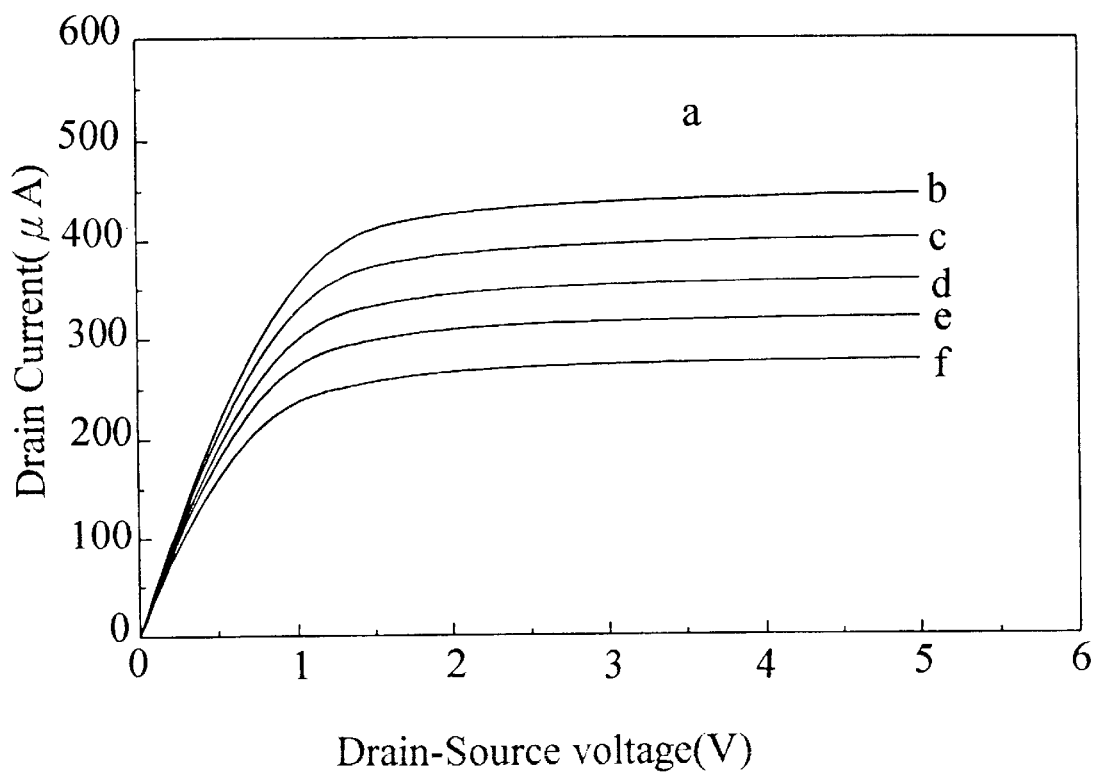
FIG. 3 shows the current-voltage characteristics of $SnO_2/SiO_2$ gate sensing device of the present invention.

FIG. 3 shows the current-voltage characteristics of $SnO_2/SiO_2$ double-layer ion sensitive field effect transistor in the aqueous solution of pH2, pH4, pH6, pH8, pH10 when the voltage of the reference electrode at operating point is kept at 1V. As shown in this figure, this device will generate different threshold voltage after different testing solutions contact with sensing membrane. Therefore, the current will vary with different solutions for the purpose of detection.

Figure 4:
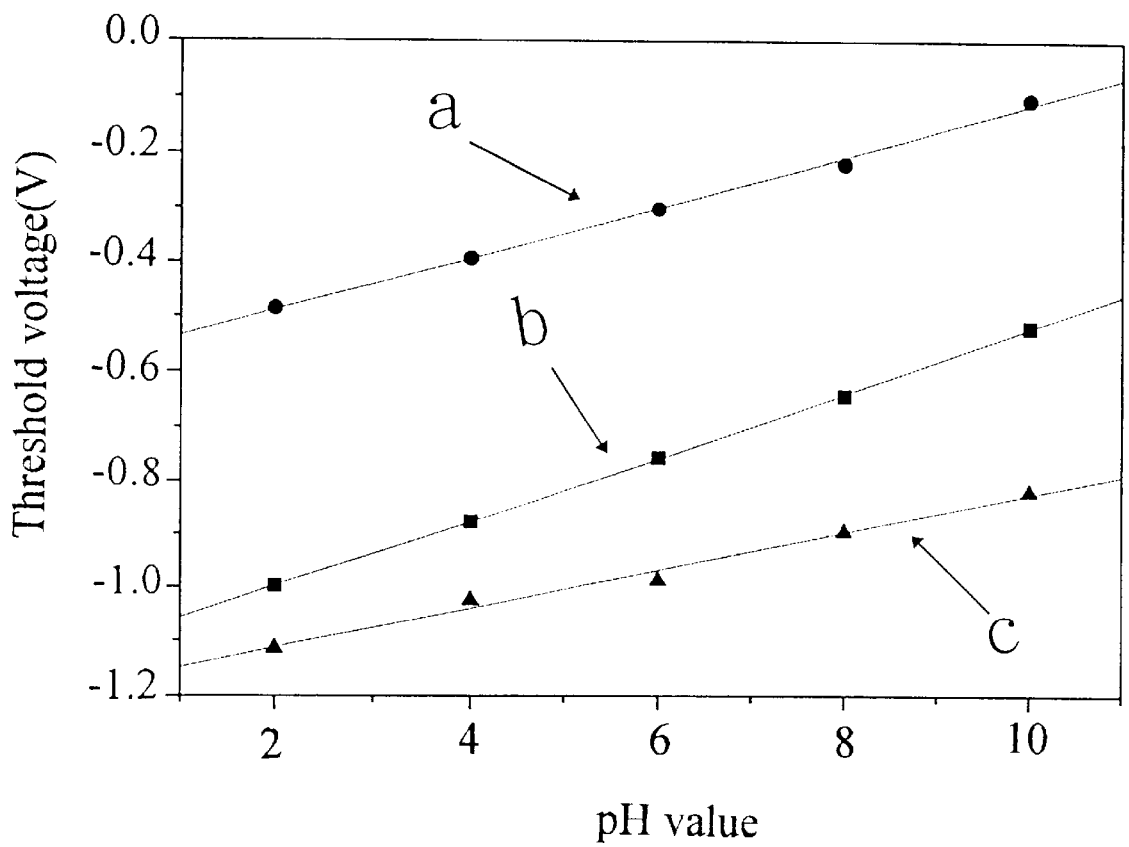
FIG. 4 shows the characteristics of three sensing devices for comparison according to the present invention.

FIG. 4 compares the sensitivity of $SnO_2/SiO_2$ double layer ion sensitive field effect transistor, the sensitivity of the comparison set $SiO_2$ single layer ion sensitive field effect transistor, and $Si_3N_4/SiO_2$ double layer ion sensitive field effect transistor. The result shows that the sensitivity of ion sensitive field effect transistor on $SnO_2$ membrane can be as high as 58 mV/pH and it has good linearity, obviously it's better than sensing devices based on $SiO_2$ membrane (36 mV/pH) and silicon nitride membrane (47 mV/pH).

Figure 5:
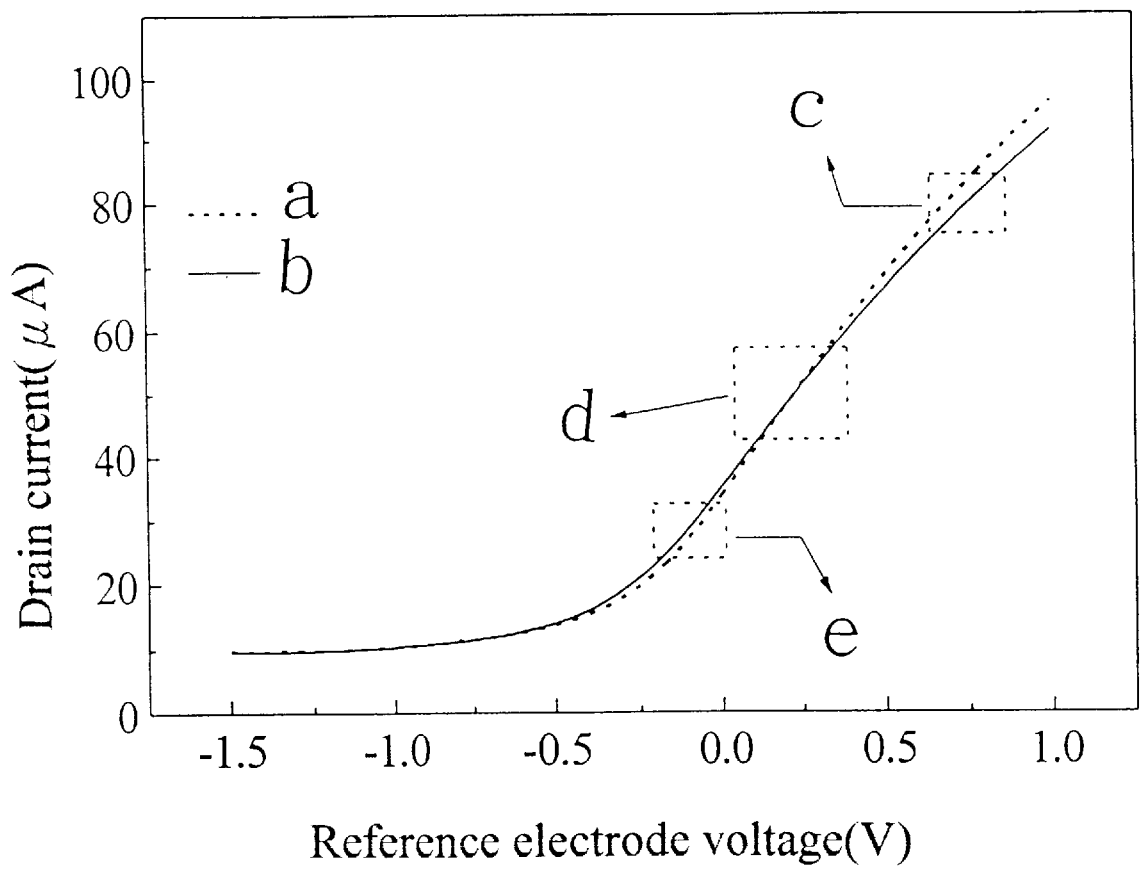
FIG. 5 shows the temperature characteristics of $SnO_2/SiO_2$ gate sensing device of the present invention.

FIG. 5 shows that the ion sensitive field effect transistor with $SnO_2$ sensing membrane can have lowest temperature coefficient at an appropriate operating point (set voltage to be 0.2V, drain current to be about 50 $\mu A$).

Figure 6:
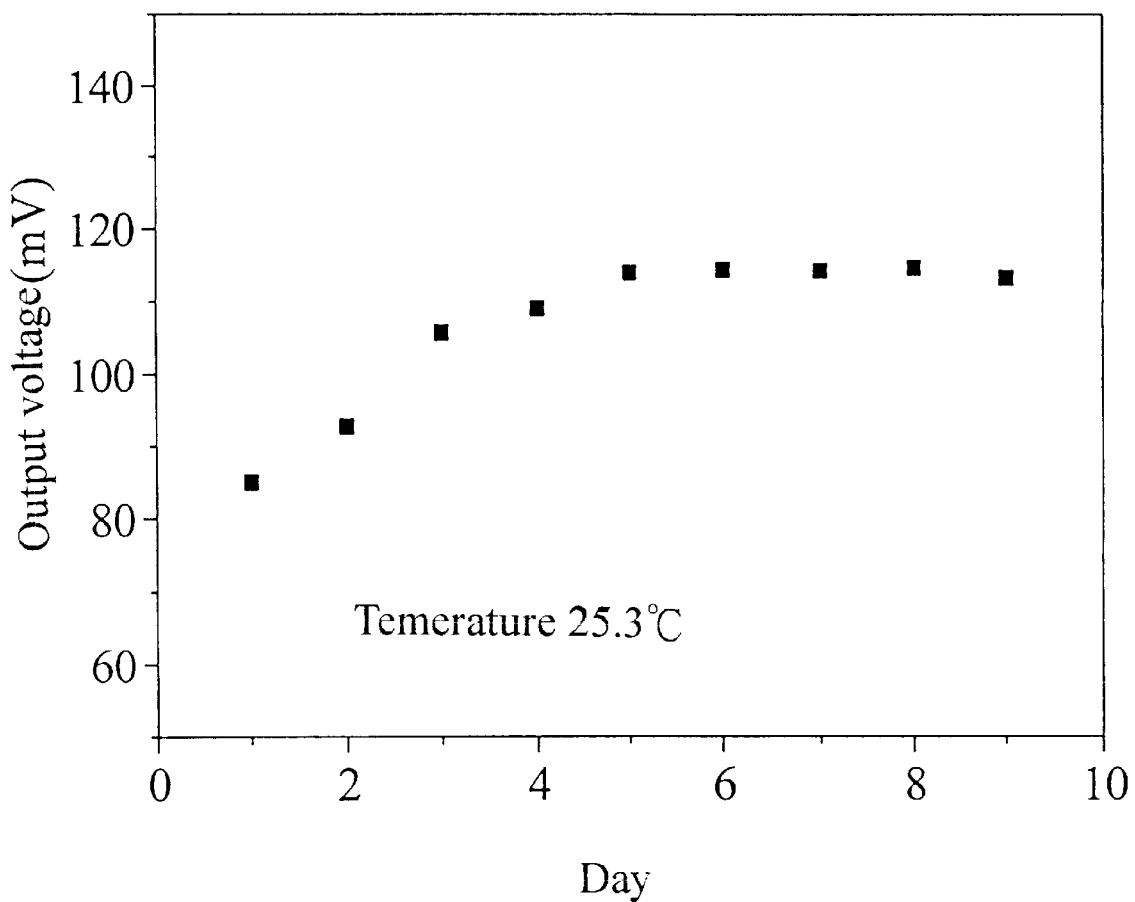
FIG. 6 shows the measured long-term stability of $SnO_2/SiO_2$ gate sensing device of the present invention.

FIG. 6 shows that the long-term stability of the ion sensitive field effect transistor with $SnO_2$ sensing membrane. The average drift voltage is 5 mV/day (which corresponds to 0.086 pH/day) during this time interval of measurement.

Figure 7:
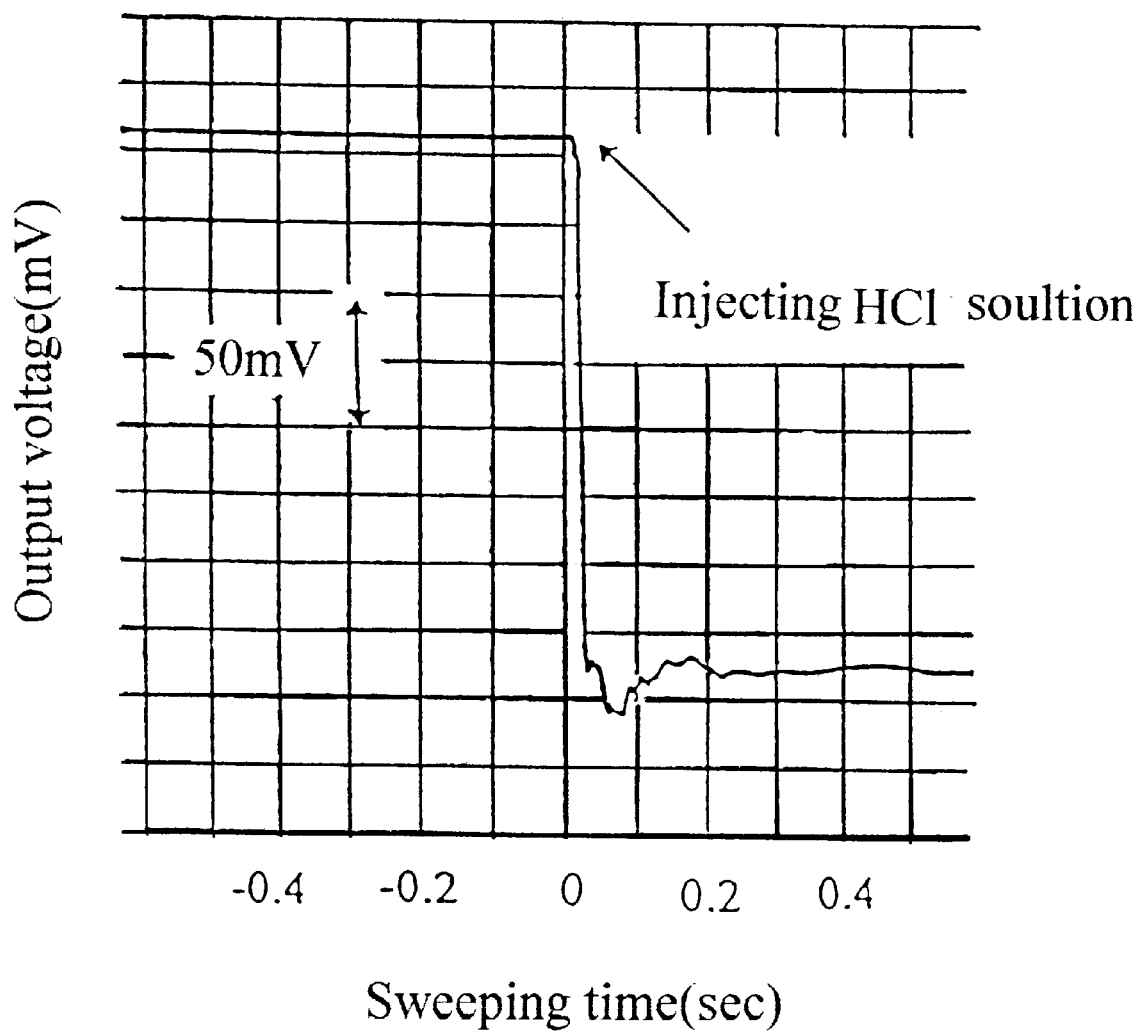
FIG. 7 shows the measured reaction rate of $SnO_2/SiO_2$ gate sensing device of the present invention.

FIG. 7 shows that the measured reaction rate of the ion sensitive field effect transistor with $SnO_2$ sensing membrane when the pH of the aqueous solution varies. As the result shows, the reaction rate of this device is very good, about shorter than 0.1 sec.

Table 4 shows the effect of annealing to $SnO_2$ membrane in nitrogen ambient. As the result shows, the sensitivity of the device is the best (about 58 mV/pH) when the annealing temperature is between 200°~300° C.

The present invention has excellent sensitivity, linearity and stability which are much better than those of traditional well-known hydrogen sensing membrane, and it is more advanced, practical and novel. What has been described is one of the embodiments of the present invention. However, the structural feature of the present invention is not confined within this embodiment. Those familiar with this technology can easily change or modify it without departing from the spirit and field of the present invention; all of these are covered in the essentials and scope of the present invention.

TABLE 1

| Parameters | Conditions |
| --- | --- |
| Deposition Rate | ~14 Å/sec |
| Background Pressure | $6 \times 10^{-6}$ torr |
| Substrate Temperature | Room temperature, 100° C., 150° C., 200° C. |
| Powder purity | 99.9% |
| Thickness | 150~200 nm |

TABLE 2

| Parameters | Conditions |
| --- | --- |
| Deposition Rate | ~20 Å/sec |
| Deposition Pressure | 20m torr |
| Background Pressure | $3 \times 10^{-6}$ torr |
| $Ar/O_2$ ratio | 4:1 |
| Substrate Temperature | Room temperature, 100° C., 150° C., 200° C. |
| Thickness | 150~200 nm |

TABLE 3

| Sample | Temperature | Time (hr) |
| --- | --- | --- |
| #1 | 200° C. | 1 |
| #2 | 300° C. | 1 |
| #3 | 400° C. | 1 |
| #4 | 500° C. | 1 |
| #5 | 500° C. | 5 |
| #6 | 500° C. | 10 |
| #7 | 500° C. | 15 |

TABLE 4

| | $SnO_2/SiO_2$ gate Sensitive Device | |
| --- | --- | --- |
| Sample | Annealing condition | Sensitivity |
| #1 | 200° C. For 1 hour | ~58.2 mV/pH |
| #2 | 300° C. For 1 hour | ~57.9 mV/pH |
| #3 | 400° C. For 1 hour | ~47.2 mV/pH |
| #4 | 500° C. For 1 hour | ~36.7 mV/pH |
| #5 | 500° C. For 5 hours | ~38.2 mV/pH |
| #6 | 500° C. For 10 hours | ~37.8 mV/pH |
| #7 | 500° C. For 15 hours | ~33.1 mV/pH |

What is claimed is:

1. A method of fabricating a multi-structure ion-sensitive field-effect-transistor from a high pH-sensing membrane of tin oxide ($SnO_2$) film to sense the concentration of hydrogen ions in solution, said method comprising the steps of:

fabricating a metal-oxide-semiconductor field effect transistor (MOSFET) structure on a p-type semiconductor substrate having an exposed gate insulator without a metal gate; and forming a tin oxide ($SnO_2$) film on the exposed gate insulator by thermal evaporation.

2. The method according to claim 1, wherein substrate temperature during said thermal evaporation is from room temperature to 200° C. and the tin oxide film is annealed in nitrogen, oxygen or argon gas.

3. The method according to claim 1, wherein substrate temperature during said thermal evaporation is from room temperature to 200° C. and the tin oxide film is annealed in oxygen.

4. The method according to claim 1, wherein substrate temperature during said thermal evaporation is from room temperature to 200° C. and the tin oxide film is annealed in argon gas.

5. A method of fabricating a multi-structure ion-sensitive field-effect-transistor from a high pH-sensing membrane of tin oxide ($SnO_2$) film to sense the concentration of hydrogen ions in solution, said method comprising:

fabricating a metal-oxide-semiconductor field effect transistor (MOSFET) structure on a p-type semiconductor substrate having an exposed gate insulator without a metal gate; and forming a tin oxide ($SnO_2$) film on the exposed gate insulator by r.f. sputtering.

6. The method according to claim 5, wherein substrate temperature during said r.f. sputtering is from room temperature to 200° C. and the tin oxide film is annealed in nitrogen.

7. The method according to claim 5, wherein substrate temperature during said r.f. sputtering is from room temperature to 200° C. and the tin oxide film is annealed in oxygen.

8. The method according to claim 5, wherein substrate temperature during said r.f. sputtering is from room temperature to 200° C. and the tin oxide film is annealed in argon gas.

9. A method of fabricating a multi-structure ion-sensitive field-effect-transistor from a high-pH-sensing membrane of tin oxide ($SnO_2$) film to sense the concentration of hydrogen ions in solution, said method comprising the steps of:

fabricating a metal-oxide-semiconductor field effect transistor (MOSFET) structure on a p-type semiconductor substrate having an exposed gate insulator without a metal gate wherein said gate insulator is about 100 nm thick;

forming a silicon nitride layer of about 100 nm thickness on the exposed gate insulator; and forming a tin oxide ($SnO_2$) film on the exposed gate insulator or on the silicon nitride.

10. The method according to claim 9, wherein said step of forming said tin oxide ($SnO_2$) film is by thermal evaporation to a thickness of about 150 to 200 nm.

11. The method according to claim 9, wherein said step of forming said tin oxide ($SnO_2$) film is by r.f. sputtering to a thickness of about 150 to 200 nm.

* * * * *